United States Patent
Semechkin et al.

(10) Patent No.: US 10,172,890 B2
(45) Date of Patent: Jan. 8, 2019

(54) TOPICAL SKIN CARE COMPOSITIONS AND METHODS

(76) Inventors: Andrey Semechkin, Rancho Santa Fe, CA (US); Nikolay A. Turovets, Carlsbad, CA (US); Larisa S. Agapova, Moscow (RU); Russell A. Kern, Rancho Santa Fe, CA (US); Jeffrey D. Janus, San Diego, CA (US)

(*) Notice: Subject to any disclaimer, the term of this patent is extended or adjusted under 35 U.S.C. 154(b) by 0 days.

(21) Appl. No.: 13/196,824

(22) Filed: Aug. 2, 2011

(65) Prior Publication Data

US 2012/0195946 A1 Aug. 2, 2012

Related U.S. Application Data

(60) Provisional application No. 61/370,191, filed on Aug. 3, 2010.

(51) Int. Cl.
| | |
|---|---|
| *A61K 35/545* | (2015.01) |
| *A61K 45/06* | (2006.01) |
| *A61Q 19/06* | (2006.01) |
| *A61Q 19/08* | (2006.01) |
| *A61K 8/98* | (2006.01) |
| *A61K 31/122* | (2006.01) |
| *A61K 31/375* | (2006.01) |

(52) U.S. Cl.
CPC ............ *A61K 35/545* (2013.01); *A61K 8/982* (2013.01); *A61K 31/122* (2013.01); *A61K 31/375* (2013.01); *A61K 45/06* (2013.01); *A61Q 19/06* (2013.01); *A61Q 19/08* (2013.01)

(58) Field of Classification Search
USPC ........................................ 424/450, 581, 93.7
See application file for complete search history.

(56) References Cited

U.S. PATENT DOCUMENTS

| | | | |
|---|---|---|---|
| 6,891,081 B1* | 5/2005 | Stern et al. ...................... 800/12 |
| 2006/0182724 A1* | 8/2006 | Riordan .................... 424/93.7 |
| 2008/0206204 A1* | 8/2008 | Brevini et al. ............... 424/93.7 |
| 2008/0299091 A1* | 12/2008 | Revazova et al. ........... 424/93.7 |
| 2009/0274770 A1* | 11/2009 | Gammelsaeter et al. .... 424/581 |

FOREIGN PATENT DOCUMENTS

WO    WO-2010/093848    *    8/2010

OTHER PUBLICATIONS

Xiaoke Y, Proteomic analysis reveals higher demand for antioxidant protection in embroyonic stem cell derived smooth mucsle cells, 2006, Wiley, 6, 6437-6446.*
Lammers T, Theranostic nanomedicine, 2011, ACS Publications, 44(10), 1029-38.*
http://www.credoreference.com/entry/hmmedicaldict/lysate.*
http://www.credoreference.com/entry/hcengdict/liposome.*
http://www.credoreference.com/entry/ehsmosbymed/dispersion.*
http://www.credoreference.com/entry/webstermed/surfactant.*
http://www.xreferplus.com/entry/penguinscience/emulsion.*

* cited by examiner

*Primary Examiner* — Celeste A Roney
(74) *Attorney, Agent, or Firm* — Louis C. Paul

(57) ABSTRACT

Topical compositions containing lysate of human parthenogenetic stem cells (hpSCs), preferably within a liposomal dispersion, that reduce the visible signs of skin aging and/or cellulite.

18 Claims, No Drawings

TOPICAL SKIN CARE COMPOSITIONS AND METHODS

CROSS-REFERENCES TO RELATED APPLICATION

This application claims the priority benefit of U.S. Provisional Application Ser. No. 61/370,191 filed on Aug. 3, 2010, the contents of which are incorporated herein by reference in their entirety.

STATEMENT REGARDING FEDERALLY SPONSORED RESEARCH OR DEVELOPMENT

Not applicable.

FIELD OF THE INVENTION

The present invention relates to compositions and methods for reducing the signs of aging of the skin, including facial fine lines, wrinkles, furrows, skin laxity and decreased skin hydration. The present invention also relates to compositions and methods for reducing the appearance of cellulite.

BACKGROUND OF THE INVENTION

Chronological/intrinsic aging and extrinsically-caused stresses (e.g, exposure to ultraviolet radiation, environmental pollutants, chemicals, cigarette smoke, temperature extremes) causes human skin to exhibit superficial fine lines, wrinkles and deeper lines (also known in the art as furrows). Aging skin is characterized by loss of elasticity and recoil, impaired barrier function, increased transepidermal water loss, as well as changes in qualities and quantities of glycosaminoglycans and proteoglycans and collagen and elastic fibers (e.g., decreased number and diameter of elastic fibers in the papillary dermis).

With aging, the amount and structural integrity of dermal connective tissues, in particular collagen and elastin, are reduced. One of the most visually prominent features of aged facial skin is fine lines and wrinkles. Leyden, Br. J. Dermatol. Vol. 122, Suppl. 35, pp. 1-3 (1990). At the outset, superficial lines and wrinkles are transient, and are classified as "dynamic", appearing with the activity of facial muscles. Crow's feet around the eyes are caused by smiling and activity of the eyelid muscles (orbicularis oculi). Frown lines between the eyebrows are caused by contraction of corrugator supercilii muscles and procerus muscle. Muscle movement likewise causes marionette lines from the mouth to the chin. With time, the mechanical stress caused by repeated facial causes these temporary lines wrinkles to become visible and permanent without expression. Kligman et al, Br. J. Derm. Vol. 113, pp. 37-42 (1985). Chronic sun exposure and smoking are known to accelerate the weakening of the dermal matrix and the appearance of more persistent, then static, lines and wrinkles. Additionally, nasolabial folds, creases on the sides of the nose that extend to the corners of the mouth, deepen with age, making the face appear tired and older.

In response to the needs to reduce the appearance of facial fine lines, wrinkles and deeper lines, to make older skin tighter, to improve skin hydration (water retention) there has been a proliferation of anti-aging skin care products. There remains a need for more efficacious antiaging skin care products. The methods and compositions of the present invention meet this need.

Cellulite is a pathophysiologic condition resulting in the destruction of collagen in the pelvic region, lower limbs (legs about four inches above the knees), and abdomen in the majority of post-pubertal women. Although its etiology of cellulite is not fully understood, cellulite thought to be caused by the herniation of subcutaneous fat within fibrous connective tissue. Cellulite presents as "orange peel" texture and dimpling and is often accompanied by stretch marks. A recent review article in the Journal of the American Academy of Dermatology reported that currently available treatments for cellulite are only partially or temporarily effective. M H Khan et al., J. Am. Acad. Dermatol. Vol. 62, pp. 361-370 (March 2010). Thus, there remains a need for more efficacious cellulite-reducing topical compositions. The present invention addresses this need.

SUMMARY OF THE INVENTION

The methods of the present invention relate to topical compositions that include lysate of human parthenogenetic stem cells (hpSCs) that are cultivated with or without feeder cells in a culture medium that, in preferred embodiments, is free of xenoreagents.

DETAILED DESCRIPTION OF THE INVENTION

Unless otherwise recited or required by the context, percent and "%" refer to percent by weight.

As used herein in connection with a measured quantity, "about" refers to a variation in the measured quantity that would be expected by the skilled artisan performing the measurement and exercising a level of care commensurate with the objective of the measurement and the equipment used; and includes rounding errors.

Essential to the topical compositions useful in the practice of the methods of the present invention is a lysate of human stem cells that is obtained from parthenogenetically activated human oocytes. Stem cells from parthenogenetically activated human oocytes (referred to as hpSCs) differ from human embryonic stem cells from normally-fertilized oocytes. The alleles found near the centromeres of the DNA and at the distal ends of the DNA of heterozygous hpSCs exhibit a larger than average homozygosity than do somatic cells derived from the oocyte donor. Comparative analysis of single nucleotide polymorph markers shows that hpSCs display a lower proportion of heterozygosity near both the centromeres and the telomeres in comparison with the heterozygosity in the intervening regions, as compared to human embryonic stem cells activated with contribution of a male gamete. Because there is no male gamete, there is no imprinting patterns donated by the male genome no "paternal imprinting").

Parthenogenetic activation of human oocytes to obtain hpSCs can be carried-out according to the method described in U.S. Pat. No. 7,732,202 and U.S. Patent Application Publication No. 2008/0299091, incorporated herein in its entirety by reference. However, other methods of parthenogenetic activation of human oocytes are known and can be employed to obtain the hpSCs useful to make the hpSC lysate essential to the composition and method of the present invention. For example, the oocyte may be activated by chemical, mechanical, and/or electrical methods known in the art. Important is that the activation of the oocyte be accomplished without participation of a male gamete. However, the parthenogenetic oocyte activation methods in U.S. Pat. No. 7,732,202 and U.S. Patent Application Publication No. 2008/0299091 are preferred methods for parthenogenetic activation of human oocytes to obtain the hpSCs useful in obtaining the hpSC lysate of the compositions and methods of the present invention. The hpSC lysate can be derived from one or more human parthenogenetic stem cell lines.

Parthenogenetically activated human oocytes are cultured, preferably in a non-xenogenic medium, until a quantity of cells sufficient to an isolate inner cell mass (ICM) that, in turn, provides the hpSCs that are cultured to obtain the cells from which the hpSC lysate useful in the practice of the present invention is obtained. Isolation of the ICM can be done mechanically, or by immune surgery to remove the trophectoderm, to provide the hpSCs for further propagation and processing according to processes described below to obtain the hpSC lysate useful in the practice of the present invention.

Importantly, the hpSCs from which the hpSC lysate is obtained are cultured in a culture vessel in feeder-free medium that, in preferred embodiments, is non-xenogenic medium. That is, hpSCs are cultivated without feeder cells, for example fibroblasts, in a medium that preferably does not include compositions from a mammal that is other than a human, i.e., in non-xenogenic medium. A combination of Dulbecco's modified Eagle medium and Ham's medium, supplemented with minimal essential medium (including non-essential amino acids), further augmented with Ham's fibroblast growth factor and human Actavin A is an example of a nonxenogenic medium useful in cultivating the hpSCs employed to obtain the hpSC lysate useful in the practice of the present invention. Reference to hpSC medium in the remainder of this description will be understood to mean culture medium that, in preferred embodiments, is free of xenoreagents.

To obtain a volume of hpSCs sufficient to obtain the desired quantity of hpSC lysate, preferably in non-xenogenic medium, equilibrated before use at 37° C. in an atmosphere of 5% $CO_2$/5% $O_2$ or under ambient conditions (about 21% $O_2$) is used. Culture media, preferably free of xenoreagents, useful in cultivating hpSCs from which the lysate can be obtained are known in the art. An example of a suitable cell culture medium is as follows:

Knockout™ D-MEM/F12 (Gibco)
15% Knockout™ Serum Replacement XenoFree (Gibco)
GlutaMAX-1 (Gibco) 100×
MEM NEAA (Gibco) 200×
2-Mercaptoethanol (Gibco) 1000×
5 ng/ml Human FGF-basic (PeproTech)
20 ng/ml Recombinant human Activin A (R&D Systems)

hpSCs from blastocyst ICM are passaged into hpSC culture medium contained in a culture vessel. The culture vessel in this step and in all steps in the method is passivated with human serum, removed from the culture vessel before passaging. Prior to first passaging, the culture vessel and hpSC are incubated at 37° C. (5% $CO_2$/5% $O_2$). The first passage cells are incubated ca. 30 min, the medium is separated, and the cells washed in situ with calcium- and magnesium-free PBS. The cells are then treated with collagenase type IV at 37° C. (5% $CO_2$/5% 30 $O_2$).

The collagenase is separated and the remaining cells washed with calcium- and magnesium-free PBS, after which hpSC is introduced to the culture vessel. Cells are divided 1:3, passaged into passivated culture vessels, and incubated (ca. 7 days) in hpSC medium at 37° C. (5% $CO_2$/5% $O_2$). Cells are divided, passaged, and cultivated (ca. 7 days) in hpSC medium until a desired volume of hpSC is obtained.

To harvest and lyse the hpSCs, hpSC culture medium is removed from the culture vessel(s) and cells are trypsinized with non-animal origin trypsin replacement enzyme. TrypLE™ available from Gibco (LifeTechnologies Corp., Carlsbad Calif.). The replacement enzyme is subsequently neutralized with hpSC culture medium that, importantly, is free of proteinase inhibitors. Harvesting and lysing of hpSCs without use of proteinase inhibitors is an important feature of the present invention. The hpSC lysate may, and in preferred embodiments is, formed without detergent agents. Still more preferably, the hpSC lysate is formed by sonicating the hpSCs or repeated freeze/thaw cycles.

Following neutralization of the trypsin replacement enzyme, the hpSCs and conditioned medium are centrifuged to pellet the cells and, importantly, supernatant conditioned medium is separated from the pellet. The pelleted cells are suspended in isotonic solution, incubated, and subjected to three or more, preferably 4 or more freeze (liq. $N_2$)—thaw cycles. The resulting suspension is centrifuged and the supernatant that is the hpSC lysate of the present invention is separated, free of conditioned medium. The hpSC lysate can be used immediately, or cryostored (e.g., −80° C.) until used.

The lysate can be applied directly to the skin to reduce the signs of ageing discussed above, or it can be, and in preferred embodiments is, encapsulated or contained within liposomes that are present with other components in a topical composition.

Liposomes are microscopic spherical vesicles formed by hydrating phospholipids, including lecithins, phosphatidyl ethanol amines, or sphingomyelins. In the compositions of the present invention, liposomes phospholipids and cholesterol in the various ratios including (but not limited to) 7:3, 5:1, 50:1. Phospholipids are from natural origin including (but not limited to) eggs and soybean.

Methods of preparing liposomes are well known in the art. Generally, under low-sheer mixing in water, the phospholipids arrange themselves in multi-lamellar sheets of concentric phospholipid spheres in a hydrophilic head-to-head and hydrophobic tail-to-tail configuration. It is well-known to persons having skill in the art that liposomal vesicles can be designed to entrap and deliver (at desired rates of release) specific active ingredients by varying the lipid content, size, surface charge and method of preparation. The liposomes can sized within a desired particle size range and particle size distribution by methods known in the art. For example, cationic charged liposomes may be prepared by incorporating stearylamine as a charged lipid into a formulation. Nonionic and anionic charged liposomes may be prepared by altering the molarity of dipalmitoylphosphatidylglycerol as the charged lipid. See also, e. g, M. Rosen, ed., Delivery System Handbook for Personal Care and Cosmetic Products: Technology, Applications and Formulations, pp. 285-303 (William Andrew, 2005).

Liposomes typically contain about 5-15 mole percent of negatively charged phospholipids, such as phospatidylglycerol, phosphatidylserine or phospatidylinositol. (Negatively charged phospholipids help prevent aggregation of the liposomes.) In preferred embodiments of the present invention, liposome suspensions are formulated to include agents that protect the lipids of the skin as well as the lipid components of the liposomal vesicles from free-radical and lipid-peroxidative damage (e.g., during storage). Non-limiting examples of such lipid-protective agents include fat-soluble antioxidants, such as tocopheryl acetate, retinyl palmitate, butylated hydroxytoluene, butylated hydroxyanisole, ascorbyl palmitate and mixtures thereof.

The lecithins useful in obtaining the lecithin-liposome encapsulated hpSC lysate useful in the practice of the present invention are phospholipids that are fatty acid diesters of the choline ester of glycerophosphoric acid. Such fatty acid diesters of the choline ester of glycerophosphoric acid are commonly referred to as phosphatidyl cholines. Soy lecithin is a preferred fatty acid diester of the choline ester of glycerophosphoric acid for use in the practice of the present invention, but other phosphatidyl cholines can be used.

The hpSC lysate used in the compositions and methods of the present invention, when contained within liposomes, is prepared by lysing from about 500,000 to about 10,000,000 hpSCs/24 ml of liposomal dispersion.

In embodiments of the present invention directed to topical anti-aging compositions, the hpSC lysate, whether or not within a liposomal dispersion, is present in an amount effective to reduce or improve one or more of the signs of skin aging, including depth and number of facial fine lines and wrinkles, skin laxity and/or skin hydration. In topical anti-aging compositions, hpSC lysate is preferably present within a liposomal dispersion at a concentration of on the order of $1 \times 10^3$ to $1 \times 10^9$ cells per gram of liposomal dispersion, still more preferably on the order of from $1 \times 10^4$ to $1 \times 10^8$ cells per gram of liposomal dispersion.

In embodiments of the present invention directed to topical anti-cellulite compositions, the hpSC lysate, whether or not within a liposomal dispersion, is present in an amount effective to reduce the appearance of orange-peel texture, dimpling and/or stretch marks on areas affected with cellulite and/or to reduce the appearance of fine lines and wrinkles superimposed on the orange-peel/dimpling characteristic of cellulite. In topical anti-cellulite compositions, hpSC lysate is preferably present within a liposomal dispersion at a concentration of on the order of $1 \times 10^3$ to $1 \times 10^9$ cells per gram of liposomal dispersion, still more preferably on the order of from $1 \times 10^4$ to $1 \times 10^8$ cells per gram of liposomal dispersion.

The hpSC lysate of the compositions and methods of the present invention can be used alone or, in preferred embodiments, in combination with further pharmaceutically and cosmetically acceptable ingredients. In a preferred embodiment, the hpSC lysate is in combination with a mixture of Coenzyme Q10 and a tocopherol ($\alpha$-, $\beta$-, or $\gamma$-), especially $\alpha$-tocopherol (vitamin E), or a tocotrieneol ($\alpha$-, $\beta$-, $\gamma$-, or $\Delta$-) or mixture a of tocopherols ($\alpha$-, $\beta$-, and/or $\gamma$-), and, optionally, one or more tocotrieneols ($\alpha$-, $\beta$-, $\gamma$-, and/or $\Delta$-). The mixture of coenzyme Q and tocoperol(s) and/or tocotrieneol(s) (the coenzyme Q combination) can be, and in particularly preferred embodiments is, encapsulated or contained in liposomes.

In this preferred embodiment, the hpSC lysate is further in combination with a mixture of bioflavonoids (flavonoids, isoflavonoids, and neoflavonoids), also referred to herein as vitamin P. Flavonoids, isoflavonoids and neoflavonoids are natural products derived from 2-20 phenylchromen-4-one (flavone), 3-phenylchromen-4-one and 4-phenylcoumarin, respectively.

In particularly preferred embodiments, the bioflavonoid is isoquercetin, troxerutin or mixtures thereof.

In further particularly preferred embodiments, the composition and method of the present invention further employs a vitamin B complex, hyaluronic acid, and an ascorbate, preferably magnesium ascorbyl phosphate.

The vitamin B complex can be any combination of compounds understood by the skilled artisan under the term "vitamin B", or their salts. A preferred vitamin B complex includes iinositol, choline chloride, calcium D-pantothenate, nicotinamide, folic acid pyridoxal hydrochloride, thiamine hydrochloride, and riboflavin in a weight ratio of 2:1:1:1:1:1:1:0.1. The vitamin B complex can be, and in preferred embodiments is, provided and used in aqueous saline.

When used, the vitamin B complex is present at 0.05% to 5%, the hyaluronic acid is present at 0.01% to 3%, and the ascorbate is present at 0.01% to 2.5%.

In embodiments of the present invention directed to the reducing the appearance of cellulite, the topical composition to be applied to the area of skin exhibiting an orange-peel texture, dimpling and/or stretch marks comprises a hpSC lysate, preferably within a liposomal dispersion, and optionally, but preferably together with coenzyme Q combination and vitamin P, in further combination with an anti-cellulite active ingredient. By anti-cellulite active ingredient is meant a skincare active ingredients that functions as an antioxidant, reduces edema, reduces inflammation, stimulates lipolysis, improves/increases microvascular perfusion, promotes production of collagen and/or elastins. Non-limiting examples of anti-cellulite active ingredients include: theophylline and its derivatives; and carnitine and its derivatives; proanthocyanidins; extracts of *Centella asiatica*; ursolic acid; and *Ginkgo biloba* dimeric flavonoids; and *Coleus forskolii* extract.

The compositions and methods of the present invention, both anti-aging and anticellulite, can further employ additional ingredients, common in the art, that do not affect the functioning of the composition or the results achieved by practice of the method.

The International Cosmetic Ingredient Dictionary and Handbook published by the Personal Care Products Council (formerly the Cosmetic, Toiletry, and Fragrance Association) describes a wide variety of non-limiting cosmetic and pharmaceutical ingredients commonly used in cosmeceutical products, which are suitable for use in the topical anti-aging compositions and anti-cellulite compositions and related methods of the present invention.

In embodiments of the present invention directed to a topical anti-aging composition to be applied when the user is exposed to ambient sunlight, the composition preferably contains at least one of a UVA sunscreen, a UVB sunscreen, and still more preferably at least one UVA sunscreen and at least one UVB sunscreen. By "UVB sunscreen" is meant chemical that absorbs, reflect, or scatter ultraviolet radiation having wavelengths from 290 to 320 nm. By "UVA sunscreen" is meant chemical that absorbs, reflect, or scatter ultraviolet radiation having wavelengths from 320 to 400 nm.

The UVA or UVB sunscreen may be selected from the group consisting of: p-Aminobenzoic acid up to 15%; Avobenzone up to 3%; Cinoxate up to 3%; Dioxybenzone up to 3%; Homosalate up to 15%; Menthyl anthranilate up to 5%; Octocrylene up to 10%; Octylmethoxycinnamate (Octinoxate) up to 7.5%; Octyl salicylate up to 5%; Oxybenzone up to 6%; Padimate O up to 8%; Phenylbenzimidazole sulfonic acid (Ensulizole) up to 4%; Sulisobenzone up to 10%; Titanium dioxide up to 25%; Trolamine salicylate up to 12%; Zinc oxide up to 25%. Other sunscreens approved in countries outside the U.S. are also suitable for inclusion in compositions according to this aspect of the invention.

In embodiments of the present invention directed to a topical anti-aging composition to be applied when the user is not exposed to ambient sunlight (e.g., in the evening prior to bed), composition further comprises a retinoid selected from the group consisting of: retinol, retinal, retinol esters, retinyl propionate, retinoic acid, retinyl palmitate.

In certain preferred embodiments the topical anti-aging compositions and/or anti-cellulite compositions of the present invention include one or more natural moisturizing factors (NMFs), ingredients that help to prevent or minimize transepidermal water loss. Non-limiting examples of NMFs that may be employed in the composition and method of the present invention include amino acids, ceramides, hyaluronic acid, cholesterol, fatty acids, triglycerides, phospholipids, glycosphingolipids, urea, linoleic acid, glycosaminoglycans, glycerin, mucopolysaccharide, and sodium PCA. Additionally, in such embodiments, the compositions of the present invention can, and preferably do include, one or more dermal lipomimetic(s), by which is meant an ingredient that mimics the lipid content of the skin. Non-limiting examples of dermal lipomimetic ingredients include apricot oil, canola oil, coconut oil, corn oil, jojoba oil, jojoba wax, lanolin, lecithin, olive oil, safflower oil, sesame oil, shea butter, soybean oil, and sweet almond oil.

The compositions of the present invention can be provided and used in any physical dosage form known in the dermatological and cosmetic arts for topical administration of active ingredients or medicaments. For example, the composition of the present invention can be provided and applied to skin in the form of a cream, a lotion, a gel, a serum or a spray that can be in the form of a single-phase dispersion, preferably a thickened aqueous dispersion, or an emulsion (e.g., oil-in-water, water-in-oil, silicone-in-water, water-in-silicone).

Formulation and compounding of these forms is well known in the art and described, for example, in M L Schlossman, ed. Chemistry and Manufacture of Cosmetics, $4_{th}$ Ed. The hpSC lysate, optionally but preferably together with coenzyme Q combination and vitamin P, and additional ingredients, is formulated and compounded with the desired delivery vehicle, or the required components thereof, in such proportions that, when applied, a dosage sufficient to (i) reduce the appearance of the fine lines and/or wrinkles, (ii) increase skin elasticity and firmness, (iii) improve skin hydration and, in the case of anti-cellulite compositions, reducing the appearance orange-peel texture and dimpling, particularly on the thighs. In the method of the present invention, the dosage form is applied at least once, preferably more that once, in a 24-hour period.

One aspect of the present invention is directed to a method for reducing the appearance of aging, in particular, a reduction in superficial fine lines (SFLs) and wrinkles, by applying the compositions of the present invention to areas of the face, neck (décolleté) and hands exhibiting signs of aging. Reduction in SFLS and wrinkles can be assessed using methods known to persons having skill in the art, including by clinical testing using a method described by Packman and Gans in "Topical Moisturizers: Quantification of their Effects on Superficial Facial Lines," J. Soc. Cosmet. Chem. Vol. 29, pp. 79-90 (1978).

In a "wash out" period (e.g., one week prior to entering the study), subjects discontinue use of other skin care products and are given a bar of mild soap with which to wash their face. (This "skin equilibration" creates a baseline value and helps to minimize possible confounding from previous skin care regimens.) On the first day after the one-week skin equilibration, all study participants are given instructions on how to use the test product (i.e., the composition of the present invention). Subjects are instructed to wash their face with the mild soap as provided for the remainder of the study. At two weeks, four weeks and eight weeks, depth, shallowness and the number of SFLs are scored within a defined area around the eye.

Reduction in SFLs as well as wrinkles can also be measured and assessed through clinical photography (using standardized lighting and positioning aids to ensure reproducibility) and image analysis software, including, for example, VISIA Complexion Analysis from Canfield Scientific. Additionally, improvement in the appearance of fine lines and wrinkles can be assessed by taking Silflo replicas at baseline and at the end of a study and measuring changes in the levels of shadows generated by incident lighting at the surface of Silflo replicas.

Another aspect of the present invention is directed to a method of improving skin firmness by applying the compositions of the present invention to the face or other areas exhibiting skin laxity. Skin firmness can be assessed using methods known in the art including by using a ballistometer, a device that drops a pendulum on the skin surface and measures the height of first and second rebound peaks.

A still further aspect of the present invention is directed to a method for improving the skin hydration (also expressed as improved retention of water or skin moisture content) by applying to the face, hands and other surfaces of the body exposed to the environment (i.e., without being covered by an article of clothing) the compositions of the present invention.

Skin moisture content can be assessed via impedance measurements on the cheek area of subjects using a Novameter. By way of non-limiting example, at the end of a one week skin equilibration period (as described above) two separate measurements are taken on each subject and averaged.

In embodiments of the present invention directed to reducing the appearance of cellulite a clinical study is conducted, with evaluations at baseline, then at 2 weeks, 4 weeks and 8 weeks 20 days. Color photographs are taken at these intervals of the outer thigh, from hip to knee. Additionally, close-up photographs are taken of the skin on the thigh, to show fine lines and wrinkles superimposed on the orange-peel/dimpling characteristic of cellulite. Skin looseness is assessed with calipers. Skin firmness and resilience are measured by a ballistometer. Subjects also provide a self-assessment of cellulite severity and improvement. The present invention, in certain of its embodiments, is illustrated by the following nonlimiting examples.

Example 1—Preparation of hpSC Lysate hpSC Culture Medium:
  Knockout™ D-MEM/F12 (Dulbecco's modified Eagle Medium+Ham's Medium—Gibco)
  15% Knockout™ Serum Replacement XenoFree (Gibco)
  GlutaMAX-1™ (Gibco) 100×
  MEM NEAA (Gibco) 200×
  2-Mercaptoethanol (Gibco) 1000×
  5 ng/ml Human FGF-basic (PeproTech)
  20 ng/ml Recombinant human Activin A (R&D Systems)
Non-Xenogenic Reagents:
  TrypLE (trypsin replacement enzyme; Gibco)
  PBS w/o $Ca_{2+}Mg_{2+}$
  Collagenase Type IV (Gibco) solution (1500 Units/ml)
  KCl solution (0.075 M) (Sigma)
Maintenance and Passaging of hpSCs with Collagenase:
1) Equilibrate hpSC culture medium, PBS, collagenase at +37° C., 5% $CO_2$, 5% $O_2$ humidified atmosphere.
2) 30 minutes prior to hpSC passaging, aspirate human serum from Petri dish (100 mm) that has been conditioned overnight with human serum; add fresh hpSC culture medium to dish now coated with serum proteins (8 mL hpSC culture medium 20 per one Petri Dish 100 mm). Place dish in incubator at +37° C., 5% $CO_2$, 5% $O_2$, humidified atmosphere.
3) After 30 minutes, aspirate hpSC culture medium from Petri dish containing passaged hpSC colonies.
4) Wash cells twice in situ with PBS without $Ca_{2+}Mg_{2+}$ (4 mL/Petri dish 100 mm).
5) Add 4 mL of collagenase type IV and incubate at +37° C., 5% $CO_2$, 5% $O_2$, humidified atmosphere for 6-8 minutes.
6) As soon as the first signs of curling at the edges of the colonies are observed, remove collagenase and wash cells with PBS without $Ca_{2+}Mg_{2+}$ (4 mL/Petri dish 100 mm).
7) Add 3 mL hpSC culture medium per Petri dish (100 mm).
8) Detach cells with 1000 μL Pipet to break up clumps of cells by pipetting gently. The final clumps of cells should each contain a few hundred cells.
9) Split cells 1:3.
10) Plate cells onto Petri dishes preliminarily conditioned with human serum.
11) Incubate dishes at +37° C., 5% $CO_2$, 5% $O_2$, humidified atmosphere.
12) Replace the hpSC culture medium every day. Split the cells 1:3 in 7 days.

In 7 days after the second passaging of hpSC using feeder-free culture system cells are ready to be lysed.

Preparation of hpSC Lysate:
1) Calibrate hpSC culture medium, TrypLE (Gibco) and hypotonic solution (0.075 M 15 KCl) at +37° C., 5% CO2, 5% O2, humidified atmosphere.
2) Aspirate hpSC culture medium from the dish with colonies of cells and add 3 ml of TrypLE per dish (100 mm) and incubate at +37° C., 5% $CO_2$, 5% $O_2$, humidified atmosphere for 1-2 minutes.
3) Neutralize TrypLE with hpSC culture medium (5 mL/Petri dish 100 mm).
4) Triturate the cell clumps using a sterile 5 mL pipette and place cell suspension into a 15 mL conical centrifuge tube.
5) Count the amount of cells using hemocytometer.
6) Pellet the cells by centrifugation for 3 min at 300×g.
7) Remove the supernatant from centrifuge tube.
8) Re-suspend pellet in 1 mL of hypotonic solution per $5 \times 10^6$ cells and incubate at +37° C., 5% $CO_2$, 5% $O_2$, humidified atmosphere for 30-40 minutes.
9) Cryofreeze cell suspension (using liquid nitrogen), thaw in water bath at 37° C. Repeat freeze-thaw three times. Alternatively, or in addition, the suspension may be sonicated.
10) Transfer solution in 1.5 mL plastic sterile centrifuge tubes and centrifuge it at 9,000×g, 4 C for 5 minutes.
11) Transfer supernatant in new 1.5 mL plastic sterile centrifuge tubes and freeze it at −80° C. Store at −80° C. until use.

Example 2—Night Anti-Aging Cream

| Phase A | Stearic Acid Soap | 0.50-5.00 |
|---|---|---|
| | Fatty Alcohol | 0.50-4.00 |
| | Glyceryl Monostearate | 1.00-4.00 |
| | Sorbitan Oleate | 0.20-2.50 |
| | Polysorbate 80 | 0.20-2.50 |
| | Safflower Oil | 0.50-2.00 |
| | Retinyl Palmitate | 0.10-0.30 |
| Phase B | Carbomer | 0.10-0.70 |
| | Preservatives | 0.50-3.00 |
| | Glycerin (or Other Humectants) | 0.50-5.00 |
| | Chealating Agent (e.g., EDTA) | 0.02-0.08 |
| | Hyaluronic Acid | 0.05-1.00 |
| | Sodium PCA | 0.10-1.00 |
| Phase C | Liposomal Dispersion of hpSC Lysate of Example 1 | 3.00-8.00 |
| | Liposomal Emulsion containing Coenzyme Q10 + Vitamin E | 2.00-6.00 |
| | Bioflavonoids | 1.00-3.00 |
| | B Vitamin Complex | 0.50-4.00 |

Example 3—Daytime Moisturizing Anti-Aging Lotion with Sunscreen

| Phase A | Stearic Acid Soap | 0.50-5.00 |
|---|---|---|
| | Fatty Alcohol | 0.50-3.00 |
| | Glyceryl Monostearate | 1.00-3.50 |
| | Sorbitan Oleate | 0.20-2.50 |
| | Polysorbate 80 | 0.20-2.50 |
| | $C_{12}$-$C_{15}$ Alkyl Benzoate | 2.00-8.00 |
| | Safflower Oil | 0.50-4.00 |
| | Octyl methoxycinnamate | 3.00-7.00 |
| | Avobenzone | 1.00-3.00 |
| | Oxybenzone | 2.00-6.00 |
| Phase B | Carbomer | 0.10-0.70 |
| | Preservatives | 0.50-3.00 |
| | Glycerin (or Other Humectants) | 0.50-5.00 |
| | Chealating Agent (e.g., EDTA) | 0.02-0.08 |
| | Magnesium Ascorbyl Phosphate | 0.25-1.00 |
| Phase C | Liposomal Dispersion of hpSC Lysate of Example 1 | 3.00-8.00 |
| | Liposomal Emulsion containing Coenzyme Q10 + Vitamin E | 2.00-6.00 |
| | Bioflavonoids | 1.00-3.00 |
| | B Vitamin Complex | 0.50-4.00 |
| | Vitamin $D_3$ | 0.01-0.50 |

The formulations in Examples 2 and 3 are made by combining and heating, in separate vessels, the ingredients in Phases A and B thereby creating, respectively, the oil and water phases of an emulsion. Both phases can be heated to about 75° C. Phase A is added to Phase B. The resulting NB mixture is mixed at 75° C. with a Silverson homomixer (of similar mixing device known to persons having skill in the art) until homogenous and is then allowed to cool. At about 38° C., Phase C is added to A/B and mixed with a sweep mixed with low shear until homogenous.

We claim:
1. A method for improving one or more signs of skin aging by (i) reducing the depth or number of facial fine lines and wrinkles or (ii) increasing skin elasticity or firmness or (iii) improving skin hydration comprising the step of applying to the skin a topical composition comprising a lysate of human parthenogenetic stem cells, wherein lysate of human parthenogenetic stem cells (hpSCs) is produced by a process comprising the steps of (a) passaging and then incubating hpSCs from blastocyst inner cell mass in cell culture medium, (b) separating the hpSCs from the cell culture medium and washing the hpSCs with calcium- and magnesium-free phosphate based saline (c) treating the hpSCs with collagenase type IV, (d) separating the collagenase from hpSCs, (e) washing the hpSCs with calcium- and magnesium-free phosphate based saline and (f) harvesting and lysing the hpSCs.

2. The method of claim 1 wherein the topical composition further comprises at least one antioxidant.

3. The method of claim 2 wherein the at least one antioxidant is selected from the group consisting of Coenzyme Q10 and its analogs, ascorbic acid and its salts, ascorbyl esters of fatty acids, tocopherol and its esters, butylated hydroxybenzoic acids and their salts, and retinoids.

4. The method of claim 1 wherein the lysate of human parthenogenetic stem cells is present in the topical composition within a liposomal dispersion.

5. The method of claim 4 wherein the lysate of human parthenogenetic stem cells is present within a liposomal dispersion at a concentration of from $1\times10^3$ to $1\times10^9$ human parthenogenetic stem cells per one gram of liposomal dispersion.

6. The method of claim 5 wherein the liposomal dispersion further comprises at least one lipid-protective agent.

7. The method of claim 6 wherein the lipid-protective agent is a fat-soluble antioxidant selected from the group consisting of tocopheryl acetate, retinyl palmitate, butylated hydroxytoluene, butylated hydroxyanisole, ascorbyl palmitate and mixtures thereof.

8. The method of claim 7 wherein the topical composition further comprises one or more of a second antioxidant, a vitamin or vitamin derivative, or a short-chain, elastin/collagen stimulating peptide.

9. The method of claim 1 or 4 wherein the human parthenogenetic stem cells are cultured in feeder-free medium.

10. The method of claim 8 wherein the human parthenogenetic stem cells are harvested and lysed without the use of proteinase inhibitors.

11. The method of claim 1 or 4 wherein the topical composition further comprises Coenzyme Q10 and vitamin E or a derivative thereof.

12. The method of claim 4 wherein the liposomal dispersion containing the lysate of human parthenogenetic stem cells is present in the topical composition at 1% to 20% by weight of the composition.

13. The method of claim 12 wherein the topical composition further comprises a B vitamin complex.

14. The method of claim 13 wherein the topical composition comprises (a) 1% to 20% by weight of a liposomal dispersion containing the lysate of human parthenogenetic stem cells (b) Coenzyme Q10 and vitamin E or a derivative thereof (c) a vitamin B complex;

(d) vitamin P.

15. The method of claim 14 wherein the topical composition further comprises one or more of a retinoid, a natural moisturizing factor, a dermal lipomimetic or a sunscreen.

16. A method of reducing the appearance of cellulite by applying to the skin of a postpubertal woman exhibiting "orange peel" texture, dimpling or stretch marks a topical composition comprising a lysate of human parthenogenetic stem cells wherein lysate of human parthenogenetic stem cells (hpSCs) is produced by a process comprising the steps of (a) passaging and then incubating hpSCs from blastocyst inner cell mass in cell culture medium, (b) separating the hpSCs from the cell culture medium and washing the hpSCs with calcium- and magnesium-free phosphate based saline (c) treating the hpSCs with collagenase type IV, (d) separating the collagenase from hpSCs, (e) washing the hpSCs with calcium- and magnesium-free phosphate based saline and (f) harvesting and lysing the hpSCs the topical composition further comprises at least one of an anti-oxidant, an anti-edema ingredient, an anti-inflammatory, an ingredient that stimulates lipolysis, an ingredient that improves/increases microvascular perfusion, an ingredient that promotes production of collagen or elastins.

17. The method of claim 16 wherein the lysate of human parthenogenetic stem cells is present in the topical composition within a liposomal dispersion.

18. The method of claim 17 wherein the topical composition further comprises Coenzyme Q10 and vitamin E or a derivative thereof.

* * * * *